(12) United States Patent
Kim et al.

(10) Patent No.: US 11,560,460 B2
(45) Date of Patent: Jan. 24, 2023

(54) PLASTICIZER COMPOSITION, RESIN COMPOSITION AND METHOD OF PREPARING THE SAME

(71) Applicant: LG CHEM, LTD., Seoul (KR)

(72) Inventors: Hyun Kyu Kim, Daejeon (KR); Mi Yeon Lee, Daejeon (KR); Jeong Ju Moon, Daejeon (KR); Joo Ho Kim, Daejeon (KR); Seok Ho Jeong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 57 days.

(21) Appl. No.: 15/558,448

(22) PCT Filed: Jul. 22, 2016

(86) PCT No.: PCT/KR2016/008046
§ 371 (c)(1),
(2) Date: Sep. 14, 2017

(87) PCT Pub. No.: WO2017/018741
PCT Pub. Date: Feb. 2, 2017

(65) Prior Publication Data
US 2018/0066124 A1 Mar. 8, 2018

(30) Foreign Application Priority Data

Jul. 24, 2015 (KR) .......................... 10-2015-0105324
Jul. 21, 2016 (KR) .......................... 10-2016-0092874

(51) Int. Cl.
| | | |
|---|---|---|
| C08K 5/1515 | (2006.01) | |
| C08K 5/12 | (2006.01) | |
| C08K 5/101 | (2006.01) | |
| C08K 5/00 | (2006.01) | |
| C07D 303/16 | (2006.01) | |
| C08L 101/02 | (2006.01) | |
| C08L 101/06 | (2006.01) | |

(52) U.S. Cl.
CPC .......... *C08K 5/0016* (2013.01); *C07D 303/16* (2013.01); *C08K 5/101* (2013.01); *C08K 5/12* (2013.01); *C08K 5/1515* (2013.01); *C08L 101/025* (2013.01); *C08L 101/06* (2013.01)

(58) Field of Classification Search
CPC .............................. C11C 3/003; C08K 5/0016
See application file for complete search history.

(56) References Cited

U.S. PATENT DOCUMENTS

| | | | | |
|---|---|---|---|---|
| 2,485,160 A * | 10/1949 | Niederhauser | ....... | C07D 303/42 549/527 |
| 3,011,999 A | 12/1961 | Parker et al. | | |
| 2008/0318042 A1 | 12/2008 | Kusek | | |
| 2012/0085568 A1 | 4/2012 | Eaton | | |
| 2014/0309345 A1 | 10/2014 | Frenkel et al. | | |
| 2015/0112008 A1 | 4/2015 | Patil et al. | | |
| 2016/0347932 A1* | 12/2016 | Nishimura | ........... | B32B 27/304 |

FOREIGN PATENT DOCUMENTS

| | | |
|---|---|---|
| CN | 1123738 A | 6/1996 |
| CN | 103848595 A | 6/2014 |
| CN | 103975011 A | 8/2014 |
| CN | 104327483 A * | 2/2015 |
| CN | 104327483 A | 2/2015 |
| GB | 851753 A | 10/1960 |
| JP | 61243845 A | 10/1986 |
| JP | 2012-255104 A | 12/2012 |
| KR | 10-2014-0116371 A1 | 10/2014 |
| WO | WO-2015141182 A1 * 9/2015 ........... B32B 27/065 |

OTHER PUBLICATIONS

Machine Translation of CN104327483A. Feb. 4, 2015. (Year: 2015).*
Machine Translation of CN103848595A. Jun. 11, 2014. (Year: 2014).*
Weisfeld, L. B. Polymer Modifiers and Additives, Chapter 11: Plasticizers. 2001. Taylor & Francis Group, LLC. pp. 419-437. (Year: 2001).*
Johnson, R. W. et al. Carboxylic Acids, Fatty Acids from Tall Oil. Kirk-Othmer Encyclopedia of Chemical Technology. 2000. John Wiley & Sons, Inc. (Year: 2000).*
Flick, E. W. Plastics Additives: An Industrial Guide. Third Edition, vol. II. 2002, Noyes Publications. pp. 157-158. (Year: 2002).*
Schwab, P. A. and Wingrave, J. A. The Plasticizer Absorption of PVC. J. Macromol. Sci.-Phys., 1981,20(3), 429-440. (Year: 1981).*
Cadogan, D. F. and Howick, C. J. Plasticizers. Ullmann's Encyclopedia of Industrial Chemistry. vol. 27. 2012. Wiley-VCH Verlag GmbH & Co. KGaA. pp. 599-618. (Year: 2012).*
XP002782502, Database WPI, Week 201524, Thomson Scientific, AN 2015-20260R (Corresponding CN 1043274823A, published Feb. 4, 2015).
XP55487882, George R. Riser et al., "Vemolic Acid Esters as Plasticizers for Polyvinyl Chloride," Journal of The American Oil Chemists' Society (JAOCS), vol. 43, No. 7, Jul. 1, 1966, pp. 456-457.
K. C. Minsker et al., "Degradation and stability of polyvinyl chloride," Light Industry Press, May 31, 1985, pp. 199-200.
Wang Lan et al., "Polymer Materials," China Light Industry Press, Jan. 31, 2009, p. 257.

* cited by examiner

*Primary Examiner* — Stephen E Rieth
(74) *Attorney, Agent, or Firm* — Dentons US LLP

(57) ABSTRACT

The present invention relates to a plasticizer composition, a resin composition, and a method of preparing the plasticizer composition. The plasticizer composition comprising an isophthalate-based material; and an epoxy-based alkyl ester compound represented by Chemical Formula 1.

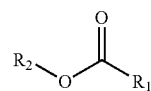

5 Claims, 1 Drawing Sheet

[FIG.1]
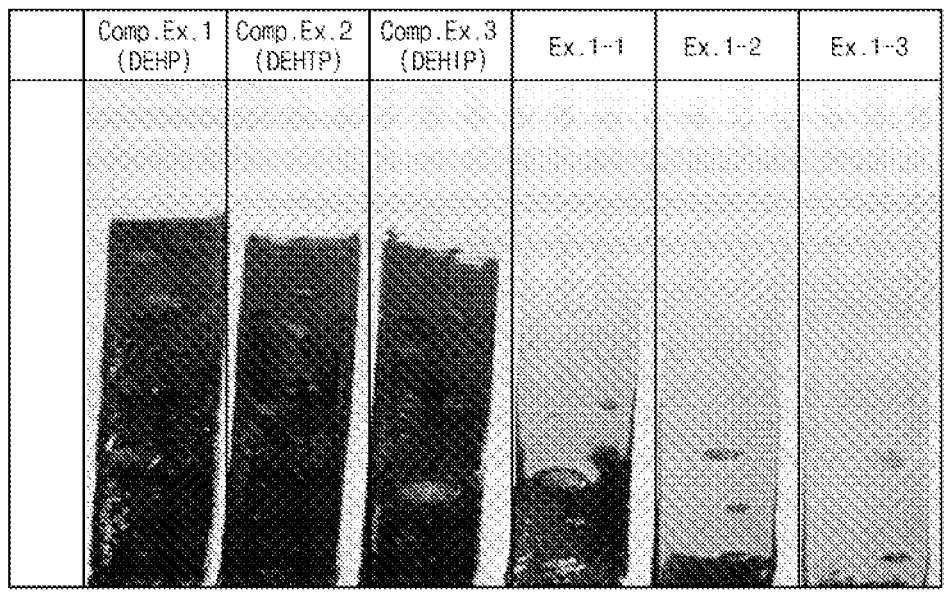
[FIG.2]
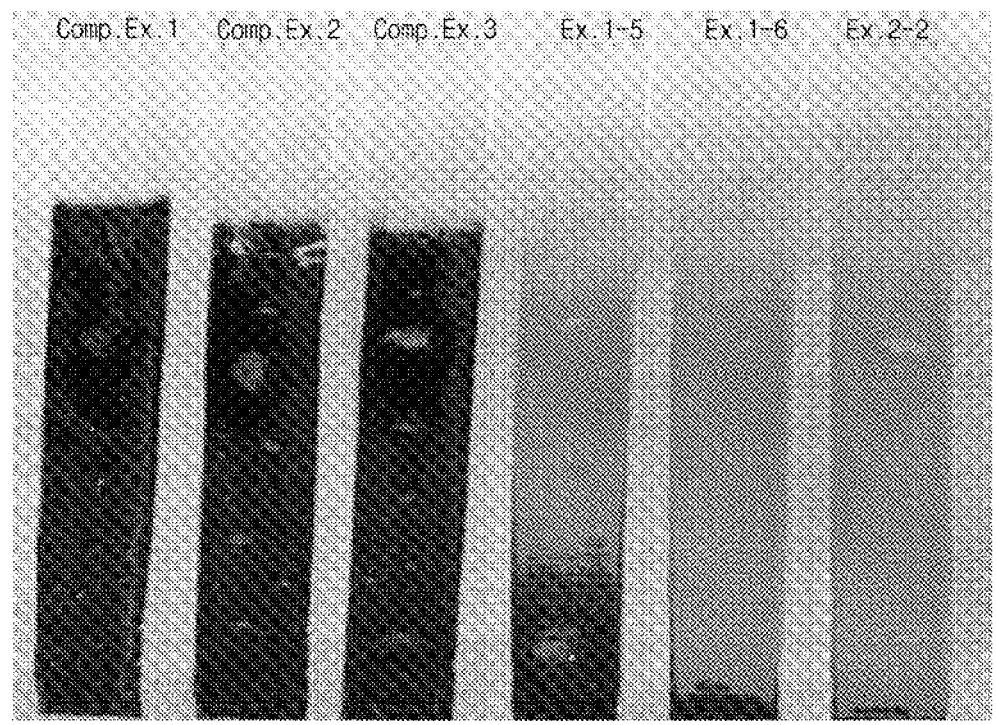

PLASTICIZER COMPOSITION, RESIN COMPOSITION AND METHOD OF PREPARING THE SAME

CROSS-REFERENCE TO RELATED APPLICATION

This application is a National Stage Entry of International Application No. PCT/KR2016/008046 filed on Jul. 22, 2016, and claims the benefit of Korean Application No. 10-2015-0105324, filed on Jul. 24, 2015, and Korean Application No. 10-2016-0092874, filed on Jul. 21, 2016, all of which are hereby incorporated by reference in their entirety for all purposes as if fully set forth herein.

TECHNICAL FIELD

The present invention relates to a plasticizer composition, a resin composition and a method of preparing the same.

BACKGROUND ART

Conventionally, a plasticizer forms an ester through a reaction between an alcohol and a polycarboxylic acid such as phthalic acid or adipic acid. In addition, in consideration of domestic and international regulations for phthalate-based plasticizers harmful to humans, there is ongoing research on plasticizer compositions that can replace phthalate-based plasticizers such as terephthalate-, adipate-, and other polymer-based plasticizers.

Meanwhile, to manufacture products such as flooring materials, wallpaper, sheets, interior and exterior materials for automobiles, films, electric wires and the like, the use of a suitable plasticizer is required in consideration of migration, volatile loss, extension, elongation, plasticizing efficiency and the like. According to properties required according to the type of industry in such various applications, i.e., tensile strength, elongation, light resistance, migration, gelation properties and the like, a PVC resin is mixed with a plasticizer, a filler, a stabilizer, a viscosity reducing agent, a dispersant, an antifoaming agent, a foaming agent or the like.

For example, among plasticizer compositions applicable to PVC, when inexpensive diethylhexylterephthalate is used, plasticizing efficiency is low, an absorption rate of the plasticizer is relatively low, and light resistance and migration are also poor.

Therefore, there is a need to develop products of a novel composition such as products with superior properties to diethylhexylterephthalate, and continuously conduct research on the most suitable technology for the use thereof as a plasticizer for vinyl chloride-based resins.

DISCLOSURE

Technical Problem

Therefore, during research on plasticizers, the present inventors verified a plasticizer composition capable of improving poor properties occurring due to structural limitations, and thus completed the present invention.

That is, an object of the present invention is to provide a plasticizer composition capable of improving properties such as plasticizing efficiency, migration, gelation properties, light resistance and the like, which are required for applications such as sheets and the like when used as a plasticizer of a resin composition, a method of preparing the same, and a resin composition including the same.

Technical Solution

According to an embodiment of the present invention, there is provided a plasticizer composition which includes an isophthalate-based material; and an epoxy-based alkyl ester compound represented by Chemical Formula 1 below, wherein a weight ratio of the isophthalate-based material to the epoxy-based alkyl ester compound is 99:1 to 1:99, and the epoxy-based alkyl ester compound is a single compound or a mixture of two or more compounds.

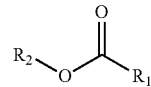

[Chemical Formula 1]

In Chemical Formula 1, $R_1$ is a $C_8$-$C_{20}$ alkyl group or an alkyl group containing one or more epoxy groups, and $R_2$ is a $C_4$ or $C_8$ alkyl group.

The weight ratio of the isophthalate-based material to the epoxy-based alkyl ester compound may be 95:5 to 5:95.

The isophthalate-based material may be di(2-ethylhexyl) isophthalate (DEHIP), diisononyl isophthalate (DINIP) or a mixture thereof.

The epoxy-based alkyl ester compound may have an iodine value of less than 4 g $I_2$/100 g.

The epoxy-based alkyl ester compound may have an epoxidation index (E.I.) of 1.5 or more.

The plasticizer composition may further include epoxidized oil.

The epoxidized oil may be included in an amount of 1 to 100 parts by weight with respect to 100 parts by weight of a mixing weight of the isophthalate-based material and the epoxy-based alkyl ester compound.

The epoxidized oil may include one or more selected from the group consisting of epoxidized soybean oil, epoxidized castor oil, epoxidized linseed oil, epoxidized palm oil, epoxidized stearic acid, epoxidized oleic acid, epoxidized tall oil, and epoxidized linoleic acid.

According to another embodiment of the present invention, there is provided a method of preparing a plasticizer composition, which includes preparing an isophthalate-based material; preparing an epoxy-based alkyl ester compound represented by Chemical Formula 1 below by performing esterification of epoxidized oil and a $C_4$ or $C_8$ primary alkyl alcohol; and mixing the isophthalate-based material and the epoxy-based alkyl ester compound in a weight ratio of 99:1 to 1:99, wherein the epoxy-based alkyl ester compound is a single compound or a mixture of two or more compounds.

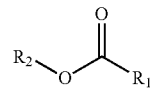

[Chemical Formula 1]

In Chemical Formula 1, $R_1$ is a $C_8$-$C_{20}$ alkyl group or an alkyl group containing one or more epoxy groups, and $R_2$ is a $C_4$ or $C_8$ alkyl group.

The primary alkyl alcohol may be one or more selected from the group consisting of butyl alcohol, isobutyl alcohol, 2-ethylhexyl alcohol and octyl alcohol.

The isophthalate-based material may be prepared through direct esterification between isophthalic acid and one or more alcohols selected from $C_4$ to $C_{12}$ primary alkyl alcohols.

The $C_4$ to $C_{12}$ primary alkyl alcohol may be one or more selected from the group consisting of 2-ethylhexyl alcohol, octyl alcohol and isononyl alcohol.

The epoxidized oil may include one or more selected from the group consisting of epoxidized soybean oil, epoxidized castor oil, epoxidized linseed oil, epoxidized palm oil, epoxidized stearic acid, epoxidized oleic acid, epoxidized tall oil, and epoxidized linoleic acid.

According to still another embodiment of the present invention, there is provided a resin composition which includes 100 parts by weight of a resin; and 5 to 150 parts by weight of the above-described plasticizer composition.

The resin may be one or more selected from the group consisting of ethylene vinyl acetate, polyethylene, polypropylene, polyketone, polyvinyl chloride, polystyrene, polyurethane, and thermoplastic elastomers.

Advantageous Effects

A plasticizer composition according to an embodiment of the present invention can provide excellent properties such as excellent plasticizing efficiency, tensile strength and an excellent elongation rate as well as excellent migration resistance, volatilization resistance and the like when used in a resin composition, and, in particular, can be suitable for use in resin products which have excellent plasticizing efficiency and an excellent high absorption rate and the like, and require environmentally-friendly plasticizers according to the use of vegetable raw materials.

DESCRIPTION OF DRAWINGS

FIG. 1 is an image showing thermal stability test results of specimens according to examples and comparative examples.

FIG. 2 is an image showing thermal stability test results of specimens according to examples and comparative examples.

MODES OF THE INVENTION

Example

Hereinafter, the present invention will be described in detail with reference to the following examples. However, the examples according to the present invention may be changed in many different forms and should not be construed as being limited to the embodiments set forth herein. Rather, these examples are provided so that this disclosure will be thorough and complete, and will fully convey the scope of the present invention to those of ordinary skill in the art.

Preparation Example 1

Preparation of di(2-ethylhexyl)isophthalate (DEHIP)

498.0 g of purified isophthalic acid (IPA), 1,170 g of 2-ethylhexyl alcohol (2-EH) (a molar ratio of IPA:2-EH=1.0:3.0), and 1.54 g (0.31 parts by weight with respect to 100 parts by weight of IPA) of a titanium-based catalyst (tetraisopropyl titanate (TIPT)) were added to a 3 L four-neck reactor equipped with a cooler, a condenser, a decanter, a reflux pump, a temperature controller, a stirrer and the like, and the temperature of the reactor was slowly raised up to about 170° C. The generation of produced water started at about 170° C., and esterification was performed at a reaction temperature of about 220° C. under an atmospheric pressure condition for about 4.5 hours while continuously introducing nitrogen gas, and was terminated when an acid value reached 0.01.

After the reaction was completed, distillation extraction was performed under reduced pressure for 0.5 to 4 hours to remove unreacted raw materials. To remove the unreacted raw materials at a predetermined amount level or less, steam extraction was performed for 0.5 to 3 hours under reduced pressure using steam. A temperature of a reaction solution was cooled to about 90° C. to perform neutralization treatment using an alkaline solution. In addition, washing could be performed, and thereafter, the reaction solution was dehydrated to remove water. A filtering material was introduced into the dehydrated reaction solution, stirred for a predetermined period of time, and then filtered, thereby finally obtaining 1,326.7 g of DEHIP (yield: 99.0%).

Preparation Example 2

Preparation of Epoxidized Fatty Acid Butyl Ester (eFABE)

500 g of epoxidized soybean oil and 490 g of butanol were used as reaction raw materials to perform trans-esterification, thereby finally obtaining 510 g of epoxidized butyl soyate (yield: 95%).

Preparation Example 3

Preparation of Epoxidized Fatty Acid 2-ethylhexyl ester (eFAEHE)

584 g of epoxidized 2-ethylhexyl soyate (yield: 95%) was obtained in the same manner as in Preparation Example 2 except that 490 g of 2-ethylhexyl alcohol was used instead of 490 g of butanol.

The materials prepared in Preparation Examples 1 to 3 were used to prepare examples and comparative examples as listed in Tables 1 to 3 below.

TABLE 1

|  | IP-based material | eFAAE material | Mixing weight ratio |
| --- | --- | --- | --- |
| Example 1-1 | DEHIP | eFABE | 7:3 |
| Example 1-2 | DEHIP | eFABE | 5:5 |
| Example 1-3 | DEHIP | eFABE | 3:7 |
| Example 1-4 | DEHIP | eFAEHE + eFABE (5:5) | 7:3 |
| Example 1-5 | DEHIP | eFAEHE | 7:3 |
| Example 1-6 | DEHIP | eFAEHE | 5:5 |
| Example 1-7 | DEHIP | eFAEHE | 3:7 |

TABLE 2

|  | IP-based material | eFAAE material | Mixing weight ratio | Third composition |
|---|---|---|---|---|
| Example 2-1 | DEHIP | eFAEHE | 7:3 | ESO (70 parts by weight) |
| Example 2-2 | DEHIP | eFAEHE | 7:3 | ESO (30 parts by weight) |

TABLE 3

|  | First composition | Second composition | Mixing weight ratio |
|---|---|---|---|
| Comparative Example 1 | DEHP | — | — |
| Comparative Example 2 | DEHTP | — | — |
| Comparative Example 3 | DEHIP | — | — |
| Comparative Example 4 | DEHIP | eFAME | 9:1 |
| Comparative Example 5 | DEHIP | eFAME | 7:3 |
| Comparative Example 6 | DEHIP | eFAME | 5:5 |
| Comparative Example 7 | DEHIP | eFAME | 3:7 |
| Comparative Example 8 | DEHIP | eFAME | 1:9 |

Experimental Example 1

Specimen Preparation and Performance Evaluation

Experimental specimens were prepared using the plasticizer compositions according to examples and comparative examples. For specimen preparation, with reference to ASTM D638, 40 parts by weight of each plasticizer composition and 3 parts by weight of a stabilizer (BZ-153T) were mixed with 100 parts by weight of PVC in a mixer at 98° C. and 700 rpm, then the resulting mixture was subjected to roll-milling at 160° C. for 4 minutes and pressed for 2.5 minutes (low pressure) and 2 minutes (high pressure) at 180° C., thereby manufacturing 1 to 3 T sheets. Each specimen was subjected to a test for properties as described below.

<Test Items>

Measurement of Hardness

According to ASTM D2240, Shore hardness (Shore "A") was measured at 25° C.

Measurement of Tensile Strength

According to ASTM D638, each specimen was pulled at a cross head speed of 200 mm/min (1T) using a tester, U.T.M, (Manufacturer; Instron, Model No.; 4466), and a position at which the specimen was broken was detected. A tensile strength was calculated as follows:

Tensile strength(kgf/cm$^2$)=Load value(kgf)/Thickness (cm)×Width(cm)

Measurement of Elongation Rate

According to ASTM D638, each specimen was pulled at a cross head speed of 200 mm/min (1T) using the U.T.M, and a position at which the specimen was broken was detected. An elongation rate was calculated as follows:

Elongation rate (%)=Length after elongation/Initial length×100

Measurement of Migration Loss

An experimental specimen having a thickness of 2 mm or more was obtained according to KSM-3156, PS plates were attached to both sides of the specimen, and then a load of 1 kgf/cm$^2$ was applied thereto. The specimen was kept in a forced convection oven (80° C.) for 72 hours, then taken out of the oven, and cooled at room temperature for 4 hours. Then, after the PS plates attached to both sides of the specimen were removed, weights before and after being kept in the oven were measured and thus a migration loss was calculated by the equation as follows.

Migration loss(%)={(Initial weight of specimen at room temperature−Weight of specimen after being kept in oven)/Initial weight of specimen at room temperature}×100

Measurement of Volatile Loss

The prepared specimen was processed at 100° C. for 72 hours, and a weight of the specimen was measured as follows.

Volatile loss(wt %)=Initial weight of specimen−(Weight of specimen after being processed at 100° C. for 72 hours)/Initial weight of specimen×100

Measurement of Absorption Rate

An absorption rate was evaluated by measuring the time taken to reach a state in which after resin and ester compounds were mixed together using a planetary mixer (Brabender, P600) at 77° C. and 60 rpm, a torque of the mixer was stabilized.

Measurement of Thermal Stability

The prepared specimens were heated to 230° C. in a Mathis oven, and combustion degrees of the specimens were measured.

Performance evaluation results of the specimens according to the above-described test items are shown in Tables 4 to 6 below, and heat resistance evaluation results thereof are illustrated in FIG. 1.

TABLE 4

|  | Hardness (Shore "A") | Tensile strength (kg/cm$^2$) | Elongation rate (%) | Migration loss (%) | Volatile loss (%) | Absorption rate (sec) |
|---|---|---|---|---|---|---|
| Example 1-1 | 84.1 | 237.2 | 326.6 | 4.02 | 3.32 | 4:35 |
| Example 1-2 | 83.0 | 233.4 | 334.5 | 3.88 | 3.70 | 3:52 |
| Example 1-3 | 81.5 | 229.7 | 324.9 | 3.76 | 4.31 | 3:27 |
| Example 1-4 | 84.7 | 240.8 | 321.5 | 3.88 | 3.25 | 4:40 |
| Example 1-5 | 85.2 | 245.0 | 317.1 | 3.68 | 3.23 | 4:55 |
| Example 1-6 | 84.9 | 244.1 | 323.7 | 3.94 | 3.30 | 4:53 |
| Example 1-7 | 84.3 | 246.1 | 320.2 | 4.16 | 3.05 | 4:28 |

TABLE 5

|  | Hardness (Shore "A") | Tensile strength (kg/cm²) | Elongation rate (%) | Migration loss (%) | Volatile loss (%) | Absorption rate (sec) |
|---|---|---|---|---|---|---|
| Example 2-1 | 84.0 | 256.7 | 324.0 | 1.21 | 1.52 | 5:08 |
| Example 2-2 | 84.5 | 250.4 | 321.6 | 1.45 | 1.88 | 4:50 |

TABLE 6

|  | Hardness (Shore "A") | Tensile strength (kg/cm²) | Elongation rate (%) | Migration loss (%) | Volatile loss (%) | Absorption rate (sec) |
|---|---|---|---|---|---|---|
| Comparative Example 1 | 86.0 | 224.6 | 287.1 | 1.75 | 5.61 | 4:50 |
| Comparative Example 2 | 88.0 | 240.3 | 306.4 | 4.12 | 2.34 | 6:31 |
| Comparative Example 3 | 87.1 | 231.9 | 305.9 | 3.86 | 3.32 | 5:50 |
| Comparative Example 4 | 83.7 | 226.3 | 304.5 | 4.23 | 4.09 | 5:05 |
| Comparative Example 5 | 82.3 | 228.0 | 305.1 | 6.56 | 5.71 | 3:20 |
| Comparative Example 6 | 80.8 | 230.1 | 305.7 | 7.98 | 7.90 | 2:35 |
| Comparative Example 7 | 79.2 | 230.9 | 308.9 | 9.34 | 9.13 | 2:03 |
| Comparative Example 8 | 78.0 | 231.7 | 309.1 | 11.87 | 12.90 | 1:43 |

Referring to Tables 4 to 6, it can be confirmed that, when compared to the specimens according to Comparative Examples 1 to 3 not including an epoxy-based alkyl ester compound, which is used as an existing general-purpose product having excellent basic properties while having problems in terms of price competitiveness, limited applications, environmental problems or the like, the specimens according to examples had almost the same mechanical properties (tensile strength and elongation rate) as those in Comparative Examples 1 to 3, exhibited a significant improvement in absorption rate or plasticizing efficiency, and also exhibited an improvement in migration loss or volatile loss.

In addition, it can be confirmed that the specimens according to Comparative Examples 4 to 8 using epoxidized methyl ester compounds not having 4 or 8 carbon atoms among epoxy-based alkyl ester compounds may exhibit an improvement in plasticizing efficiency and elongation rate, but exhibited a significant difference in migration and volatile loss according to content thereof, and also exhibited a poor level of migration and volatile loss at which it is difficult to use them. But, it can be confirmed that the specimens according to Examples 1-1 to 1-7 using $C_4$ or $C_8$ epoxidized alkyl ester compounds exhibited a significant improvement in basic properties such as tensile strength or elongation rate, in particular, volatile loss or migration loss.

From the above-described results, it can be confirmed that, when a mixture of an isophthalate-based material and an epoxy-based alkyl ester compound wherein the number of carbon atoms of an alkyl is 4 or 8 is used, mechanical properties may be improved and migration properties or volatile loss may also be significantly improved.

In addition, it can be confirmed that the specimens according to Examples 2-1 and 2-2 exhibited excellent migration loss or volatile loss as well as tensile strength and elongation rate compared to comparative examples, and exhibited further improved properties than those in Examples 1-1 to 1-7.

From the above-described results, it can be confirmed that properties may be compensated for by further using epoxidized oil.

Furthermore, referring to FIGS. 1 and 2, it can be confirmed that the specimens according to examples may exhibit an improvement in thermal stability compared to single plasticizers according to comparative examples, the specimens according to Comparative Examples 1 to 3 all were combusted and thus blackened, and the specimens according to Examples 1-1 to 1-3 and Examples 1-5, 1-6 and 2-2 exhibited significantly low combustion degrees compared to comparative examples.

Hereinafter, the present invention will be described in detail.

The terms or words used in the present specification and claims should not be construed as being limited to ordinary or dictionary meanings and should be construed as meanings and concepts consistent with the spirit of the present invention based on a principle that an inventor can appropriately define concepts of terms to explain the invention of the inventor in the best way.

The term "butyl" used herein refers to a $C_4$ alkyl group containing both a straight chain and a branched chain, and examples thereof include n-butyl, isobutyl, and t-butyl. Preferably, the butyl group is n-butyl or isobutyl.

The terms "octyl" and "2-ethylhexyl" used herein refers to a $C_8$ alkyl group, and the term "octyl" may be interchangeably used with an abbreviation for 2-ethylhexyl. In some cases, the octyl group may refer to octyl as a straight alkyl group, or 2-ethylhexyl as a branched alkyl group.

Plasticizer Composition

According to an embodiment of the present invention, there is provided a plasticizer composition which includes an isophthalate-based material; and an epoxy-based alkyl ester compound, wherein a weight ratio of the isophthalate-based material to the epoxy-based alkyl ester compound is 99:1 to 1:99, and the epoxy-based alkyl ester compound is a single compound or a mixture of two or more compounds.

The plasticizer composition including an isophthalate-based material may be provided. In particular, the isophthalate-based material may be used in an amount selected from ranges of 1 to 99 wt %, 20 to 99 wt %, 40 to 99 wt %, 50 to 95 wt %, 60 to 90 wt % and the like based on a total weight of the plasticizer composition.

The isophthalate-based material may be di(2-ethylhexyl) isophthalate (DEHIP), diisononyl isophthalate (DINIP) or a mixture thereof, and may preferably be di(2-ethylhexyl) isophthalate.

The composition ratio may be a mixed composition ratio produced by esterification and may be an intended composition ratio in which a specific compound is further mixed. The mixed composition ratio may be appropriately adjusted according to desired properties.

The plasticizer composition includes an isophthalate-based material and an epoxy-based alkyl ester compound. The epoxy-based alkyl ester compound may be represented by Chemical Formula 1 below and have an iodine value (I.V.) of less than 4 g $I_2/100$ g.

[Chemical Formula 1]

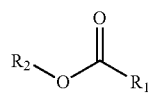

In Chemical Formula 1, $R_1$ is a $C_8$-$C_{20}$ alkyl group or an alkyl group containing one or more epoxy groups, and $R_2$ is a $C_4$ or $C_8$ alkyl group.

The epoxy-based alkyl ester compound may have an oxirane value (O.V.) of 6.0% or more, 6.3% or more, and preferably, 6.5% or more. In addition, the oxirane value may vary according to the number of epoxy groups included in a substituent denoted as $R_1$ in Chemical Formula 1, may be measured by titration, and may be measured by a method of ASTM D1562-04 using a sample and an acid solution.

In addition, the iodine value of the epoxy-based alkyl ester compound may be less than 4 g $I_2$/100 g, preferably, 3.8 $I_2$/100 g or less. The iodine value refers to the content of double bonds present in molecules, and may be obtained from values measured by titration through iodination of the double bonds.

The measured iodine value and oxirane value may be important factors when the epoxy-based alkyl ester compound is applied to the plasticizer composition. In particular, when the iodine value of the epoxy-based alkyl ester compound is 4 g $I_2$/100 g or more, compatibility of the plasticizer composition with a resin may be significantly reduced and thus the plasticizer composition may not be used as a plasticizer. When the iodine value of the epoxy-based alkyl ester compound is less than 4 g $I_2$/100 g, mechanical and physical properties such as tensile strength, elongation rate, absorption rate and the like may be improved. In addition, the oxirane value may also have a technical significance similar to that of the iodine value and may have a similar effect.

The iodine value may refer to the content of double bonds, and the content of double bonds may be the content of double bonds remaining after performing an epoxidation reaction, such as epoxidation of vegetable oil, epoxidation of fatty acid alkyl esters or the like. That is, an oxirane value and an iodine value may be indexes for a degree to which epoxidation proceeds, may be associated with each other to some extent, and may be theoretically in inverse proportion to each other.

However, double bonds of vegetable oil or fatty acid alkyl esters may substantially vary according to material, and thus the two parameters may not accurately form an inverse proportion relation or a trade-off relation, and a material with a higher iodine value among two materials may also have a higher oxirane value. Thus, the epoxy-based alkyl ester compound having iodine and oxirane values within the above-described ranges may be applied to the plasticizer composition.

Meanwhile, the epoxy-based alkyl ester compound may have an epoxidation index (E.I.) of 1.5 or more.

As described above, the iodine value and the oxirane value may satisfy the above-described relation, and, simultaneously, the epoxidation index may satisfy a range of 1.5 or more. The term "epoxidation index" as used herein refers to a ratio of oxirane value to iodine value of the epoxy-based alkyl ester compound, and may be a ratio of double bonds epoxidized by epoxidation to remaining unreacted double bonds.

As described above, when the epoxidation index is less than 1.5 due to a small amount of an oxirane or a high iodine value, or when epoxidation itself does not proceed, hardness of the plasticizer composition increases and thus a plasticizing efficiency thereof may be significantly deteriorated, and migration loss and volatile loss may also be significantly deteriorated.

In particular, the epoxidation index, which is a ratio (O.V./I.V.) of an oxirane value to an iodine value, may be 1.5 or more. That is, when a value obtained by dividing the oxirane value of the epoxy-based alkyl ester compound by the iodine value thereof is 1.5 or more, a more suitable plasticizer composition may be obtained, and, in particular, the plasticizer composition may tend to have increased compatibility with a resin.

The epoxy-based alkyl ester compound may be an epoxidized fatty acid alkyl ester (eFAAE), and, in particular, may be represented by Chemical Formula 1. "Alkyl" of the epoxy-based alkyl ester compound may have 4 or 8 carbon atoms.

However, in the present invention, $R_2$ of Chemical Formula 1 may have 4 to 8 carbon atoms, and is preferably a butyl group or a 2-ethylhexyl group. In addition, the epoxy-based alkyl ester compound represented by Chemical Formula 1 may be a mixed composition including two or more compounds, and the mixed composition including two or more compounds may be a mixture of a compound having 4 carbon atoms and a compound having 8 carbon atoms. When $R_2$ of Chemical Formula 1 has 4 or 8 carbon atoms, the plasticizer composition may have excellent absorption properties and thus exhibit less of a gelling phenomenon, may exhibit improved processability, excellent basic mechanical properties such as tensile strength or elongation rate, and, in particular, may exhibit excellent migration or volatile loss.

In this regard, a weight ratio of the isophthalate-based material and the epoxy-based alkyl ester compound included in the plasticizer composition may range from 99:1 to 1:99, 99:1 to 20:80, or 99:1 to 40:60, preferably, 95:5 to 50:50 or 90:10 to 60:40.

As described above, when the mixed plasticizer composition of an isophthalate-based material and an epoxy-based alkyl ester compound is used, excellent tensile strength and an excellent elongation rate may be obtained, improved effects in terms of migration and volatile loss may be obtained, and an absorption rate may be controlled and thus processability may also be improved.

Method of Preparing Plasticizer Composition

According to an embodiment of the present invention, there is provided a method of preparing a plasticizer composition, which includes preparing an isophthalate-based material; preparing an epoxy-based alkyl ester compound represented by Chemical Formula 1 below by performing esterification of epoxidized oil and a $C_4$ or $C_8$ primary alkyl alcohol; and mixing the isophthalate-based material and the epoxy-based alkyl ester compound in a weight ratio of 99:1 to 1:99, wherein the epoxy-based alkyl ester compound is a single compound or a mixture of two or more compounds.

The preparation of the isophthalate-based material and the preparation of the epoxy-based alkyl ester compound may be separately performed, and the materials may be prepared through direct esterification and/or trans-esterification.

The isophthalate-based material may be prepared through direct esterification between isophthalic acid and alcohols selected from $C_8$ to $C_{10}$ primary alkyl alcohols. Also, the epoxy-based alkyl ester compound may be prepared by trans-esterification between epoxidized oil and a $C_4$ or $C_8$ primary alkyl alcohol.

The $C_8$ to $C_{10}$ primary alkyl alcohol may be selected from the group consisting of 2-ethylhexyl alcohol, octyl alcohol and isononyl alcohol.

In addition, the $C_4$ or $C_8$ primary alkyl alcohol used as a raw material to prepare the epoxy-based alkyl ester compound may be one or more selected from the group consisting of butyl alcohol, isobutyl alcohol, 2-ethylhexyl alcohol, and octyl alcohol. In this case, an alkyl group of the alcohol may correspond to $R_2$ of Chemical Formula 1 in the epoxy-based alkyl ester compound represented by Chemical Formula 1 after the reaction is completed.

The epoxidized oil may be, for example, epoxidized soybean oil, epoxidized castor oil, epoxidized linseed oil, epoxidized palm oil, epoxidized stearic acid, epoxidized oleic acid, epoxidized tall oil, epoxidized linoleic acid, or a mixture thereof, and vegetable oil may be a compound into which a certain content of epoxy groups is introduced through epoxidation.

The epoxidized oil may be, for example, represented by Chemical Formula 2 below, and may contain three ester groups in a single molecule and include a certain content of epoxy groups.

[Chemical Formula 2]

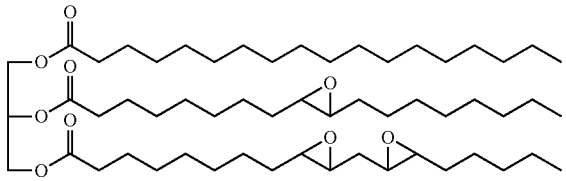

The epoxidized oil represented by Chemical Formula 2 is provided as one example.

In addition, the epoxidized oil may have an iodine value of less than 4 g $I_2$/100 g, and the iodine value is unlikely to vary during trans-esterification and thus may be almost the same as the iodine value of the epoxy-based alkyl ester compound, which is a reaction product. Characteristics of the iodine value are the same as those of the iodine value of the epoxy-based alkyl ester compound as described above.

When trans-esterification occurs between the epoxidized oil and the $C_4$ or $C_8$ alkyl alcohol, all three ester groups may be separated, and, accordingly, three or more epoxy-based ester compounds in which the alkyl group of the alcohol is newly linked may be formed.

The term "trans-esterification" used herein refers to a reaction in which, as described in Reaction Scheme 1, an alcohol reacts with an ester group and thus R″ of the ester group is interchanged with R′ of the alcohol:

[Reaction Scheme 1]

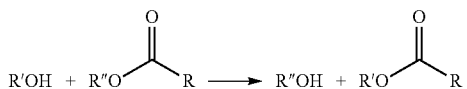

According to an embodiment of the present invention, when the trans-esterification occurs, an alkoxide of an alcohol is substituted with an ester group (RCOOR″) in an ester-based compound, and thus R″ alcohol is produced. General vegetable oil is produced by separating glycerol through a substitution reaction with an alcohol, and an ester composition having an R′ alcohol chain may be produced from a fatty acid alkyl chain. Also, the trans-esterification is advantageous in that wastewater problems are not caused and a reaction rate is high compared to an esterification between an acid and an alcohol.

Generally, a trans-esterification used to prepare an epoxy-based alkyl ester compound may be performed, for example, under conditions as follows.

The trans-esterification may be performed at a reaction temperature of 40 to 230° C., preferably 50 to 200° C., more preferably 70 to 200° C. for 10 minutes to 10 hours, preferably 30 minutes to 8 hours, more preferably 1 to 4 hours. When the reaction temperature and time are within the above ranges, a desired epoxy-based alkyl ester compound may be effectively obtained. At this time, the reaction time may be calculated from the time at which the reaction temperature is reached after heating reactants.

In addition, the method may further include removing a polyhydric alcohol and reaction byproducts produced after the trans-esterification and an unreacted alcohol through purification, washing, and distillation.

The purification process may be performed by, in particular, cooling to and maintaining at a temperature of 80 to 100° C. for a predetermined period of time after the trans-esterification. In this case, layer separation occurs wherein an upper layer may include an epoxy-based alkyl ester and an alcohol, and a lower layer may include glycerin and other byproducts. Next, to neutralize a catalyst, neutralization and washing may be induced by adding an aqueous solution for neutralizing a catalyst.

The neutralization and washing processes may be performed after, first, separating the lower layer mainly including reaction byproducts, and in the neutralization and washing processes, the byproducts included in the lower layer may be dissolved in water to be discharged, and through a subsequently repeated washing process, the unreacted alcohol and water may be recovered and removed.

However, it may be necessary to vary the neutralization and washing processes according to the number of carbon atoms of an alcohol used in the trans-esterification.

For example, in a case in which butanol with 4 carbon atoms is used, when the neutralization and washing processes are immediately performed, wastewater generation problems occur, and thus, it is preferable to previously remove butanol through distillation. However, in this case, catalytic activity remains, and thus there may be other problems, i.e., occurrence of an inverse reaction between glycerol as a reaction byproduct and an epoxy-based alkyl ester as a reaction product to produce an epoxidized oil-like material such as a diglyceride, a triglyceride or the like, and, accordingly, there is a need to pay attention to the design of manufacturing processes.

In addition, as another example, when 2-ethylhexyl alcohol with 8 carbon atoms is used, the 2-ethylhexyl alcohol has low solubility in water, and thus there is no wastewater generation problem. Accordingly, both the case of removing an alcohol after the neutralization and washing processes and the case of performing the neutralization and washing processes after removal of reaction byproducts in the lower layer may be performed without severe problems.

In addition, in the case of preparing the epoxy-based alkyl ester compound, properties of the prepared epoxy-based alkyl ester compound may vary according to the type or amount of catalyst used, and properties, yield or quality of products may vary according to reaction time or the amount of a primary alkyl alcohol reacted with epoxidized oil.

In particular, in the process of preparing an epoxy-based alkyl ester compound, NaOMe may be preferably used as a catalyst, and, when sodium hydroxide or potassium hydroxide is used as a catalyst, the color of the prepared epoxy-based alkyl ester compound may not meet its standard, and an epoxidation index, the amount of oxirane and the like of the epoxy-based alkyl ester compound may not have desired values.

In addition, the amount of the catalyst may range from 0.1 to 2.0 wt %, preferably, from 0.1 to 1.0 wt % with respect to a total weight of the epoxidized oil which is a reaction raw material. When the amount of the catalyst is within the above range, it may be most effective in terms of reaction rate, and when the amount of the catalyst is outside the above range, an epoxidation index and the like of the epoxy-based alkyl ester compound may not meet quality standards due to a failure in adjusting the amount of the catalyst.

In preparation of the epoxy-based alkyl ester compound, amounts of epoxidized oil and a primary alkyl alcohol added may be an important factor. The primary alkyl alcohol may be added in an amount of 30 to 100 parts by weight with respect to the amount of the epoxidized oil. When the amount of the primary alkyl alcohol is less than 30 parts by weight, a reaction does not occur efficiently, and thus residual epoxidized oil or impurities such as a dimerized material of epoxidized oil and the like may remain in an excess amount. Also, when the amount of the primary alkyl alcohol is 100 parts by weight or more, the amount of a residual alcohol to be separated is greater than the amount of a product in the purification process, and thus problems in terms of energy and manufacturing efficiency may occur during the process.

As described above, after preparing the isophthalate-based material and the epoxy-based alkyl ester compound, a process of mixing the two compounds may be performed. A mixing ratio may be appropriately selected from ranges from 99:1 to 1:99, and the two compounds may be mixed in the above-described mixing weight ratio.

In addition, the plasticizer composition according to the present invention may further include epoxidized oil, in addition to the isophthalate-based material and the epoxy-based alkyl ester compound.

In the case of a mixed plasticizer composition of the isophthalate-based material and the epoxy-based alkyl ester compound, thermal resistance among various properties may be relatively poor, and such thermal resistance may be compensated for by further adding the epoxidized oil.

The epoxidized oil may be, for example, epoxidized soybean oil, epoxidized castor oil, epoxidized linseed oil, epoxidized palm oil, epoxidized stearic acid, epoxidized oleic acid, epoxidized tall oil, epoxidized linoleic acid, or a mixture thereof. Preferably, the epoxidized oil may be epoxidized soybean oil (ESO) or epoxidized linseed oil (ELO), but the present invention is not limited thereto.

In addition, the epoxidized oil may be included in an amount of 1 to 100 parts by weight, preferably, 10 to 100 parts by weight, preferably, 20 to 100 parts by weight with respect to 100 parts by weight of a mixing weight of the mixture of the isophthalate-based material and the epoxy-based alkyl ester compound. When the amount of the epoxidized oil is within the above ranges, a plasticizer composition with suitably excellent mechanical properties and thermal resistance may be obtained.

Furthermore, when an isophthalate-based product and epoxidized oil are used in combination, an overall freezing point of the plasticizer composition may be further reduced, and thus the plasticizer composition has a much lower freezing point than that of an epoxy-based plasticizer composition. Therefore, a plasticizer composition without limitation on use even during the winter season may be provided.

Resin Composition

According to an embodiment of the present invention, there is provided a resin composition which includes 100 parts by weight of a resin; and 5 to 150 parts by weight of the above-described plasticizer composition.

The resin may be one or more resin selected from ethylene vinyl acetate, polyethylene, polypropylene, polyketone, polyvinyl chloride, polystyrene, polyurethane, and thermoplastic elastomers, and the plasticizer composition may be included in an amount of 5 to 150 parts by weight, 40 to 100 parts by weight, or 40 to 50 parts by weight with respect to 100 parts by weight of the resin. Therefore, a resin composition effective in compound formulation, sheet formulation and plastisol formulation may be provided.

When the resin composition includes the above-described plasticizer composition, the resin composition may be applied to a variety of applications, such as flooring materials, wallpaper, interior materials for automobiles, sheets, films, hoses, electric wires and the like, and may exhibit basic mechanical properties such as tensile strength, elongation rate, plasticizing efficiency and volatile loss that are the same as or superior to those of existing plasticizers.

According to an embodiment of the present invention, the resin composition may further include a filler.

The amount of the filler may range from 0 to 300 parts by weight, preferably, 50 to 200 parts by weight, more preferably, 100 to 200 parts by weight based on 100 parts by weight of the resin.

The filler may be any filler known in the art and is not particularly limited. For example, the filler may be a mixture of one or more selected from silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate and barium sulfate.

The resin composition may further include other additives such as a stabilizer and the like if necessary.

The amount of the other additives such as a stabilizer and the like may range, for example, from 0 to 20 parts by weight, preferably, from 1 to 15 parts by weight based on 100 parts by weight of the resin.

The stabilizer that can be used may be, for example, a calcium-zinc-based (Ca—Zn-based) stabilizer such as a Ca—Zn composite stearate or the like, but the present invention is not particularly limited thereto.

The invention claimed is:

1. A plasticizer composition for polyvinyl chloride consisting of:
   an isophthalate-based material, wherein the isophthalate-based material is di(2-ethylhexyl)isophthalate (DEHIP); and
   an epoxy-based alkyl ester compound, wherein the epoxy-based alkyl ester compound is an epoxidized butyl soyate, an epoxidized 2-ethylhexyl soyate or a mixture of an epoxidized butyl soyate and an epoxidized 2-ethylhexyl soyate,
   wherein a weight ratio of the isophthalate-based material to the epoxy-based alkyl ester compound is 70:30 to 30:70,
   wherein the epoxy-based alkyl ester compound has an iodine value of less than 4 g $I_2$/100 g, and
   wherein the epoxy-based alkyl ester compound has an epoxidation index (E.I.) of 1.5 or more.

2. The plasticizer composition of claim 1, wherein the weight ratio of the isophthalate-based material to the esterification product is 70:30 to 50:50.

3. A method of preparing the plasticizer composition for polyvinyl chloride of claim 1, comprising:
- preparing an isophthalate-based material, wherein the isophthalate-based material is di(2-ethylhexyl)isophthalate (DEHIP);
- preparing an epoxy-based alkyl ester compound, wherein the epoxy-based alkyl ester compound is an epoxidized butyl soyate, an epoxidized 2-ethylhexyl soyate or a mixture of an epoxidized butyl soyate and an epoxidized 2-ethylhexyl soyate by performing esterification of epoxidized soybean oil and butanol or 2-ethylhexyl alcohol; and
- mixing the isophthalate-based material and the epoxy-based alkyl ester compound in a weight ratio of 70:30 to 30:70;
- the epoxy-based alkyl ester compound has an iodine value of less than 4 g $I_2$/100 g, and
- the epoxy-based alkyl ester compound has an epoxidation index (E.I.) of 1.5 or more.

4. The method of claim 3, wherein the isophthalate-based material is prepared through direct esterification between isophthalic acid and 2-ethylhexyl alcohol.

5. A resin composition comprising:
100 parts by weight of a resin; and
5 to 150 parts by weight of plasticizers,
wherein the resin is polyvinyl chloride;
wherein the plasticizers consist of:
- an isophthalate-based material, wherein the isophthalate-based material is di(2-ethylhexyl)isophthalate (DEHIP); and
- an epoxy-based alkyl ester compound, wherein the epoxy-based alkyl ester compound is an epoxidized butyl soyate, an epoxidized 2-ethylhexyl soyate or a mixture of an epoxidized butyl soyate and an epoxidized 2-ethylhexyl soyate;

wherein a weight ratio of the isophthalate-based material to the epoxy-based alkyl ester compound is 70:30 to 30:70,
wherein the epoxy-based alkyl ester compound has an iodine value of less than 4 g $I_2$/100 g, and
wherein the epoxy-based alkyl ester compound has an epoxidation index (E.I.) of 1.5 or more.

* * * * *